United States Patent [19]

Baillie

[11] Patent Number: 4,761,990
[45] Date of Patent: Aug. 9, 1988

[54] METHOD AND APPARATUS FOR MEASUREMENT OF ATTRITION RATE OF PARTICULATE MATERIAL

[75] Inventor: Lloyd A. Baillie, Plano, Tex.

[73] Assignee: Atlantic Richfield Company, Los Angeles, Calif.

[21] Appl. No.: 7,318

[22] Filed: Jan. 27, 1987

[51] Int. Cl.⁴ .............................................. G01N 3/56
[52] U.S. Cl. ........................................ 73/7; 73/866; 374/31
[58] Field of Search ................ 73/866, 7; 374/32, 31

[56] References Cited

U.S. PATENT DOCUMENTS

| 3,636,772 | 1/1972 | Bennett | 73/866 |
| 4,143,539 | 3/1979 | Baillie | 73/866 X |
| 4,625,552 | 12/1986 | Johnson | 73/866 X |
| 4,633,712 | 1/1987 | Scieszka | 73/866 |
| 4,658,631 | 4/1987 | Swan et al. | 73/866 X |
| 4,702,116 | 10/1987 | Gawol et al. | 73/866 X |

Primary Examiner—Tom Noland
Attorney, Agent, or Firm—Michael E. Martin

[57] ABSTRACT

Particulate material such as fluidized bed particles, catalytic particles, and particles used in mechanical processes are measured to determine their attrition rate by providing an apparatus comprising a generally cylindrical housing having a rotary impeller disposed eccentrically in the housing for continuously agitating and impacting a quantity of particulate material being measured. A screen is formed in a sidewall of the housing and a vacuum pump is operably connected to the interior of the housing through the screen for continuously withdrawing fines generated during the attrition rate measurement process. Periodic sampling of the quantity of fines withdrawn is used to measure the mass of fines withdrawn per unit time. An equal mass of makeup material is admitted to the housing chamber after each sampling step until an equilibrium attrition rate is determined.

15 Claims, 2 Drawing Sheets

METHOD AND APPARATUS FOR MEASUREMENT OF ATTRITION RATE OF PARTICULATE MATERIAL

BACKGROUND OF THE INVENTION

1. Field of the Invention

The present invention pertains to a method and apparatus for measuring the attrition rate of particulate material such as used in fluidized bed reactors and catalyzed chemical processes, for example.

2. Background

In certain chemical processes and other manufacturing processes, masses of solid particulate material are physically moved about in such a way that the particles impact each other, or other objects, resulting in breakage and the production of smaller particles or fines. In certain chemical processes such as fluidized bed reactions and catalytic processes, the bed or catalyst material will, over a period of time, suffer an attrition of particles of proper size for continuing the reaction. In certain mechanical processes, quantities of particulate material are used in such a way that the material impacts an object and the particles of the material itself are eventually broken down into finer particles which cannot then be suitably used in the process.

Accordingly, it is desirable to know the attrition rate of various types of particulate material to determine the quality of the material and to plan maintenance operations on a quantity of the material during its use. One particularly important use of large quantities of particulate material is in the catalytic cracking of hydrocarbon fluids to produce hydrocarbons having a lower boiling point than the fluid feed stock. The catalyst material used in such processes must, from time to time, be treated to restore optimum catalytic activity by being passed through a regeneration apparatus or process, which results in mechanical degradation of the material by the formation of smaller particle or fines. The fine material is often of such a size that it cannot be reused in the chemical process and it is desirable to know the rate of attrition which will occur with a quantity of catalyst material so that proper sizing of separation equipment and a schedule of providing makeup quantities of material can be carried out. Moreover, the need to determine the quality of a particular quantity of catalyst material, or other particulate material used in processes which may result in attrition, is clearly desirable so that the material purchased can be rejected or qualified as to its use.

Various types of apparatus are available for measuring the attrition rate of particulate material. An example of a prior art apparatus is disclosed and claimed in my U.S. Pat. No. 4,143,539 which is assigned to the assignee of the present invention. However, the apparatus described in the aforementioned patent is subject to some measurement errors since the fines produced in the test apparatus are not separated from the quantity of material being tested. In this way, the constant commingling of the fines influences the attrition rate and does not give as accurate a determination of average attrition rate as is desired for certain types of measurements. Moreover, the use of such an apparatus does not conveniently provide for the determination of a so-called equilibrium rate of attrition since many samples must be analyzed in the event that one or more samples when analyzed might be samples which are not truly representative of the "hardness" or size of the material being tested.

Accordingly, there has been a continuing need for more accurate determinations of the attrition rate of certain types of particulate material such as fluidized bed reaction materials, catalyst materials used in hydrocarbon conversion processes and materials used in certain types of mechanical treatment processes, for example. In this respect, the present invention is directed to an improved apparatus for determining the average attrition rate of particulate material when subjected to its intended use. The apparatus may be used in an improved method of determining the average or equilibrium attrition rate of a particular type of particulate material.

SUMMARY OF THE INVENTION

The present invention provides an improved apparatus for determining the attrition rate of a particulate material which is subject to mechanical impacts during use. In accordance with one aspect of the present invention, an apparatus is provided which subjects a quantity of particulate material to mechanical impacts which may simulate the forces and velocities imparted to the particulate material during its intended use, whereby the rate of formation of broken particles or fines may be determined. The apparatus includes means for removing the smaller particles or fines from the quantity being tested so that the influence of the presence of the fines on the attrition rate of the test sample is avoided.

In a preferred embodiment of the apparatus, a rotary impeller is disposed in a chamber in a housing into which a sample of particulate material is deposited, and the material is agitated or circulated by the impeller to simulate the forces which would be imposed on the material during its intended use. A fluid such as ambient air is drawn through the chamber to remove the fines generated during the attrition rate test, and the quantity of fines withdrawn is weighed to determine the rate of attrition. The configuration of the housing, forming the closed chamber, includes a port through which the fines are removed. The port arranged is such that clogging of the port with fines is minimized. Fines are removed from the material being tested continuously and rapidly so as to minimize the effect of the presence of the fines on the test process.

The present invention also provides an improved method of determining the attrition rate of a quantity of particulate material whereby the average life of such material may be determined more accurately than heretofore. In accordance with one aspect of the method of the invention a quantity of particulate material is subjected to mechanical impacts to attrite the sample quantity and the fines produced are continuously removed from the quantity being attrited. An equal mass of makeup material is periodically added to the sample quantity being attrited until an equilibrium attrition rate is observed. In this way, the average attrition rate of a specific type of particulate material may be more accurately determined.

In accordance with yet another aspect of the present invention, a method for measuring the mechanical energy absorbed by the material during the attrition process may be determined calorimetrically using an improved apparatus in accordance with the present invention. Still further in accordance with the invention, an improved method of determining the average or equilibrium rate of attrition of a quantity of particulate material is determined using an improved apparatus which separates the attrited material continuously from the quantity or sample being anaylzed.

Those skilled in the art will further appreciate the abovementioned advantages and superior features of the invention, together with other aspects thereof, upon reading the detailed description which follows in conjunction with the drawing.

DESCRIPTION OF THE PREFERRED EMBODIMENTS

Figure 1:
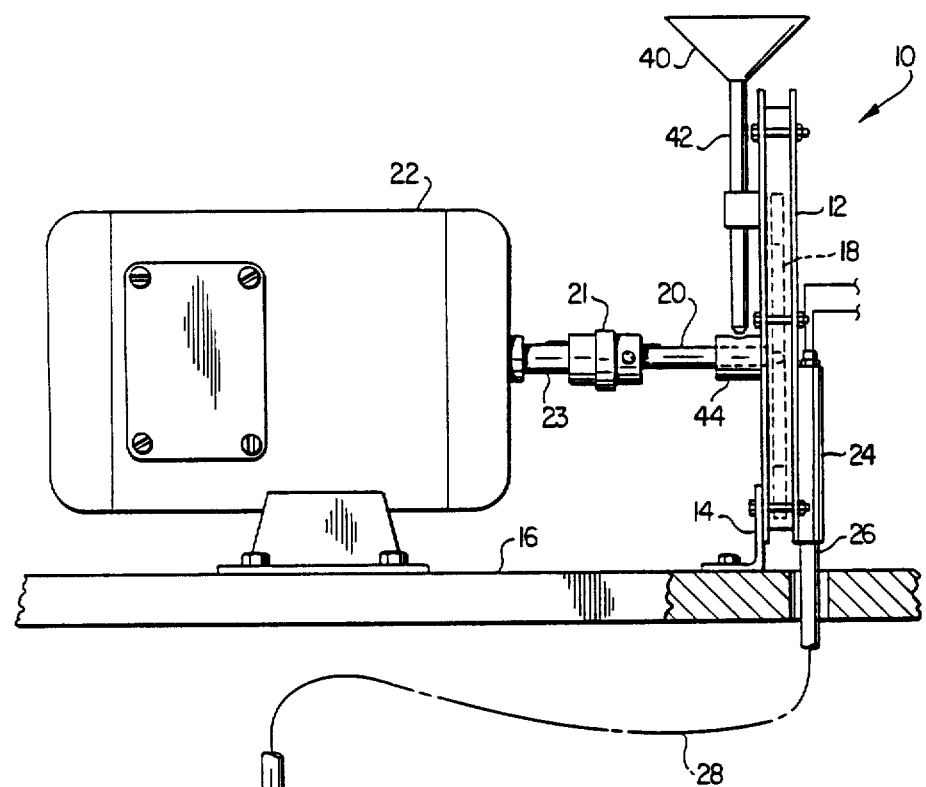
FIG. 1 is a side elevation of the improved attrition measurement apparatus of the present invention.

In the description which follows, like parts are marked throughout the specification and drawing with the same reference numerals, respectively. Certain portions of the apparatus of the invention may be shown in somewhat schematic form in the interest of clarity and conciseness.

Referring to FIG. 1, there is illustrated an improved apparatus for measuring the attrition rate of particulate material and generally designated by the numeral 10. The apparatus 10 includes a relatively thin generally cylindrical housing 12 mounted on a suitable bracket 14, which in turn is mounted on a base member 16. The housing 12 encloses a rotor 18 having a central, generally horizontally extending shaft 20 which is suitably connected to a prime mover such as a constant or variable speed electric motor 22. The motor 22 is suitably mounted on the base 16 as illustrated. The housing 12 includes a material discharge and collection portion 24 having a discharge conduit 26 extending from the bottom thereof and connected to a further conduit 28.

The conduit 28 is connected to an enclosure 30 for supporting a filter element such as conventional laboratory filter paper 32. The enclosure 30 includes separable housing portions 34 and 36 to provide access to the filter element 32 and to form an enclosure through which air having entrained therein fines of particulate material withdrawn from the housing 12 may be conducted so that the fines may be collected on the filter element 32. Suitable vacuum pump means 38 is connected to the housing 36 for drawing air through the chamber 37 formed within the enclosure 30. The source of air which flows through the chamber 37 includes the interior of the housing 12 which will be explained in further detail herein. The apparatus 10 includes suitable means for loading additional particulate material into the interior of the housing 12 comprising a material receiving funnel 40 which is mounted on the housing 12 and has a bottom outlet conduit 42 disposed to discharge material into a suitable opening formed in a hub portion 44 of the housing 12.

Figure 3:
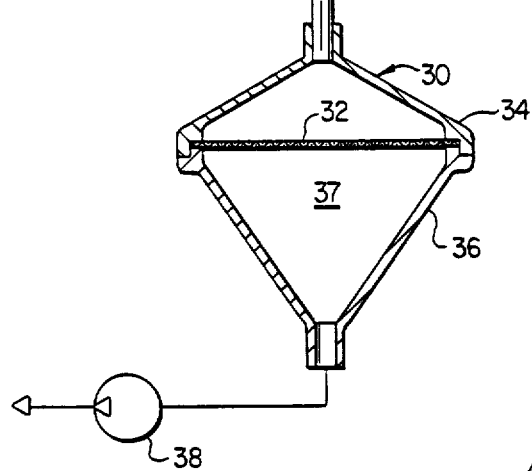
FIG. 3 is a section view taken generally along the line 3—3 of FIG. 2.
Figure 3:
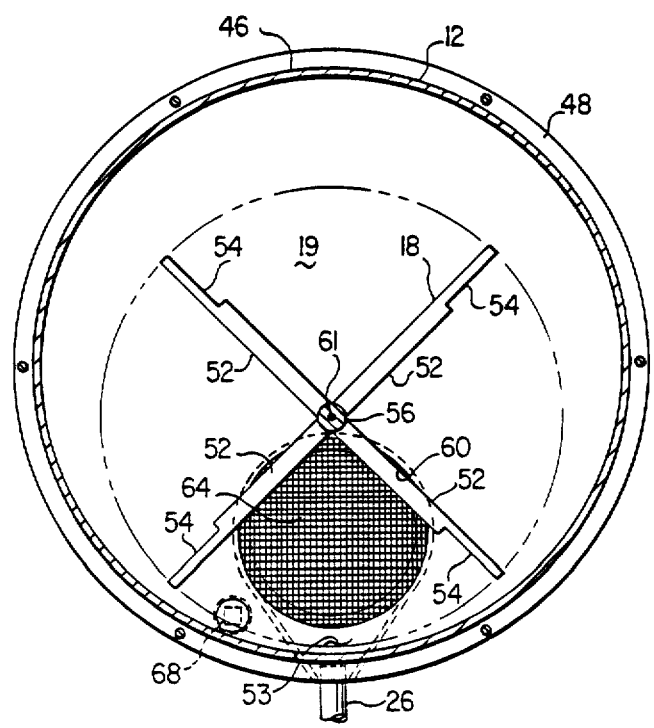
Figure 2:
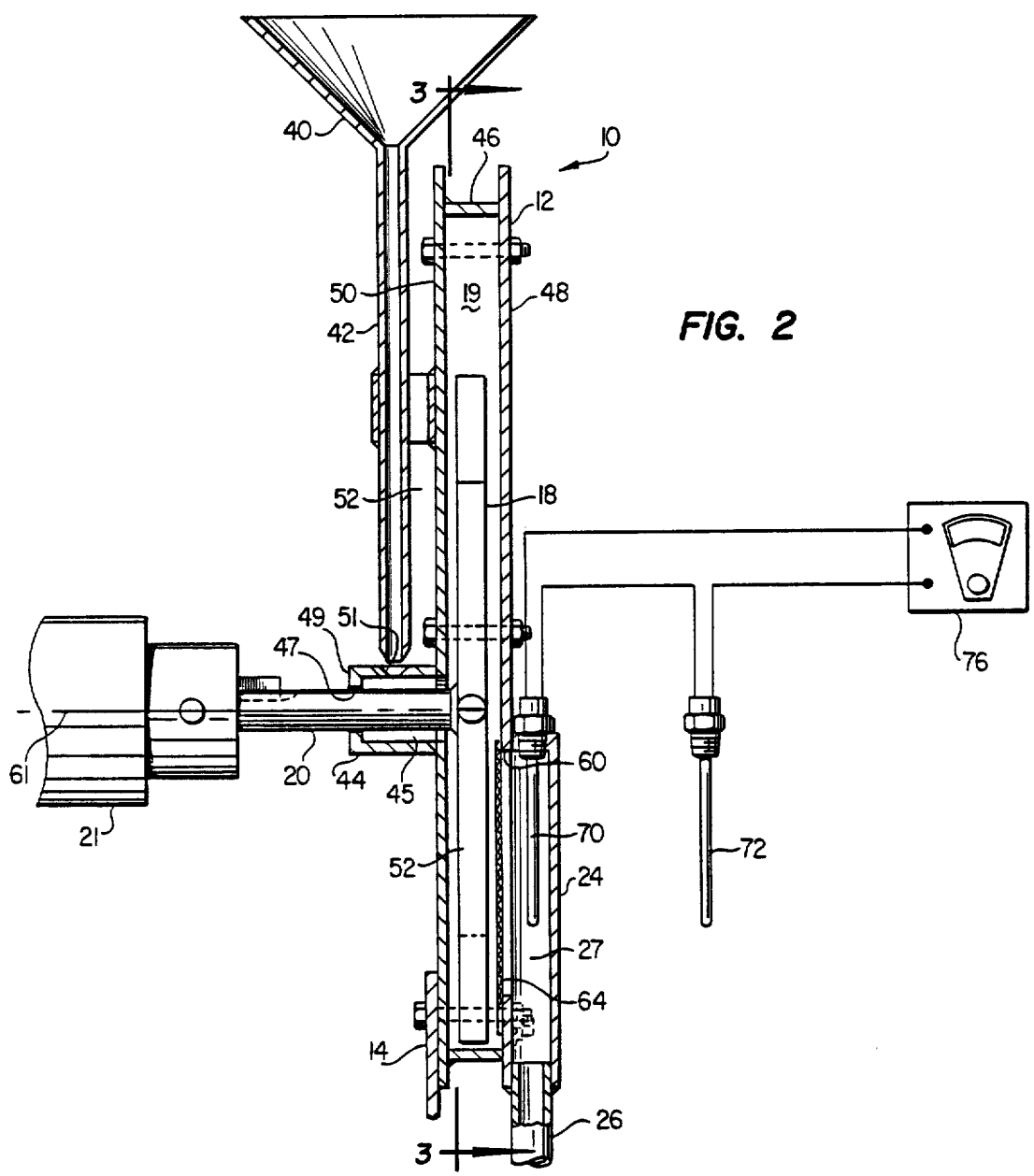
FIG. 2 is a vertical central section view through the housing and rotor of the attrition measurement apparatus.

Referring now to FIGS. 2 and 3, the housing 12 is generally cylindrical in form and includes a peripheral outer wall 46 and opposed side walls 48 and 50 which collectively define an interior chamber 19. The hub 44 is of generally cylindrical configuration and includes an interior chamber portion 45 which opens into the chamber 19. The hub 44 is somewhat eccentric with respect to the central axis of the housing 12. The rotor or impeller 18 is characterized by a plurality of radially projecting impeller blades 52 having generally flattened distal end portions 54 providing a planar surface for impacting and propelling particulate material within the chamber 19. The impeller blades 52 project from a hub portion 56 which is suitably secured to the shaft 20. The shaft 20 projects through an opening 47 formed in an end wall 49 of the hub 44 and is suitably connected to and supported by a coupling 21 connected to the motor shaft 23, see FIG. 1. The hub 44 also includes an opening 51, FIG. 3, for receiving measured quantities of makeup material from the funnel 40 during the attrition test in accordance with the method of the present invention.

The sidewall 48 is provided with a generally circular opening 60 disposed between the axis of rotation 61 of the shaft 20 and the lower portion of the chamber 19. A relatively fine mesh screen 64 is disposed across the opening 60 to prevent the discharge of particulate material except fines from the chamber 19 during an attrition rate test. As shown in FIGS. 2 and 3, the fines discharge housing portion 24 forms a chamber 27 into which the finer material formed during the attrition test is discharged from the chamber 19 through the screen 64. The material being discharged into the chamber 27 is pneumatically conveyed through the conduits 26 and 28 and impinges on the filter element 32 to be collected thereby. As shown in FIG. 3, the housing 12 may be provided with a suitable removable plug 68 disposed near the bottom of the housing to provide for removal of the particulate material remaining in the chamber 19 after a test.

As illustrated in FIG. 3, the rotor 18 is mounted such that the impeller blades 52 sweep a circular arc which is eccentric within the chamber 19 and passes relatively close to the bottom 53 of the chamber defined by the wall 46. Moreover, the impeller blades 52 also sweep an arc which envelopes the screen 64 and the impeller blades pass relatively close to the screen. Importantly, the distal ends 54 of the impeller blades 52 leave enough clearance between the blade tips and the wall 46 at their minimum clearance point to prevent crushing the largest particles of the material within the chamber 19 between the blade tips and the wall 46 so as to prevent attrition of the material from such crushing action. Still further, the close clearance between the impeller blades 52 and the screen 64 provides sufficient turbulence that particulate material which will not pass through the screen does not remain lodged on the screen during operation of the apparatus, which action would tend to clog the screen and prevent a suitable testing procedure. A more detailed description of an apparatus which has been constructed in accordance with the present invention will be given herein by way of example only.

As shown in FIG. 2, means are provided for measuring the energy imparted to the particulate material being tested, comprising a pair of thermocouples 70 and 72 which are interconnected in so called bucking relationship and are connected to a voltage measuring apparatus 76. The thermocouple 70 extends within the chamber 27 to measure the temperature of the material being discharged from chamber 19 into chamber 27 and the thermocouple 72 measures the ambient temperature in which the apparatus 10 is disposed. The thermocouples 70 and 72 may be conventional iron-constantan type thermocouples wherein the lead wires from the constantan metal portions of the thermocouples are interconnected and the lead wires for the iron portions of the thermocouples are respectively connected to the voltage measuring device 76.

The apparatus 10 should be configured to simulate the type of mechanical impacts which may be imparted to a specific type of particulate material during its intended use. Accordingly, the motor rotation speed and the length of the impeller blades 52 should be configured to provide impact velocities in the range which the particulate material would normally be expected to experience during actual use of the material. The motor speed should be maintained constant during the test process but may be selectively varied to perform different tests and provide the rotor tip speed desired.

An example of a suitable apparatus 10 for performing tests on a U.S. 260 virgin catalyst sample of the type used in petroleum refining will now be described. The exemplary apparatus preferably has a rotor made of impeller blades 52 which are approximately 0.25 inches in width and rotate within the chamber 18 to provide about 0.125 inches clearance on opposite sides of the blades with respect to the side walls 48 and 50. The diameter of the rotor 18 is approximately 6.20 inches and is adapted for rotation at approximately 3400 r.p.m. so as to provide a tip speed of the impeller blades 52 of approximately 92 feet per second. The diameter of the chamber 19 is preferably approximately 8.50 inches and the rotor shaft 20 is eccentric with respect to the central axis of the chamber so that the blade tips of the rotor 18 clear the inner surface of the wall 46 by approximately 0.125 inches at the chamber bottom side 53. The opening 60 is approximately 2.5 inches in diameter and is centered in such a way that it is enveloped by the arc of the rotor 18. The depth of the chamber 27 is preferably no more than about 0.25 inches.

An apparatus 10 having the aforementioned dimensions may be adapted to handle a cataylst sample of approximately 20 grams. Air is drawn through the chambers 19 and 27 by a vacuum pump 38 having a capacity of at least about 17 liters per minute. Air may preferably be allowed to enter the chamber 19 through clearance between the shaft 20 and the opening 47, as well as through the opening 51. Makeup catalyst may be admitted to chamber 19 through the chamber 45 in the hub 44, and makeup catalyst may be conveniently conveyed into the chamber 19 during operation of the apparatus while attrited particulate material may be continuously withdrawn from the chamber 19 through the screen 64 and the chamber 27 to be deposited on a filter element 32. For the aforementioned test, the screen 64 is preferably a 400 mesh (38 micron) type.

If calorimetric measurements are to be taken using the thermocouples 70 and 72, the apparatus 10 is allowed to run for a period of time without particulate material in the chamber 19 so that the energy imparted by the rotor 18 to the air within the chamber may provide for stabilizing the temperature of the housing 12 before tests are conducted on a sample of particulate material.

The apparatus 10 is operated in accordance with a preferred method of determining the rate of attrition of a specific type of particulate material, such as the above-mentioned catalyst, by operating the apparatus 10 to stabilize its temperature, in the event that calorimetric measurements are to be made, before adding a premeasured quantity of particulate material to the chamber 19 through to funnel 40. For example, upon commencement of a test, a 20 gram sample of particulate material is added to the chamber 19 while operating the rotor 18 at a constant speed. The material to be tested should be thoroughly prescreened using a screen of the same mesh as the screen 64. Of course, an additional quantity of material should be prescreened for use as makeup material during the test. A series of about eight or ten filter papers or elements 32 should be tared prior to commencing the test. Since most samples of particulte material are likely to contain particles with a range of attrition rates, the initial rates of fines production can be expected to be higher than the equilibrium rate. The filter element 32 should be changed during the test on a schedule such that no more than five to ten percent of the material inventory within the chamber 19 is attrited between each sampling step.

Accordingly, the apparatus 10 is operated for a predetermined period of time while drawing air through the chambers 19 and 27 to continuously withdraw the attrited fines for deposition on the filter element 32. At predetermined time intervals, the filter element 32 is removed, weighed and replaced by a clean element. An amount of particulate material equal to the mass of the attrited material collected on the filter element 32 removed during the previous test phase is then added to the chamber 19 through the funnel 40. By making repeated measurements of the type described above and plotting these measurements as total material makeup quantity versus operating time, an equilibrium or constant attrition rate will eventually be developed. The so-called equilibrium or constant material attrition rate is that which is being sought and the total mass of material tested divided by the equilibrium makeup rate yields the average age of the material in the sample. By continuously withdrawing attrited material, or fines, this material does not influence the attrition rate. Moreover, by continuously adding an amount of material equal to the weight of the fines removed after each sampling process, a constant rate of material makeup will eventually be established.

Figure 4:
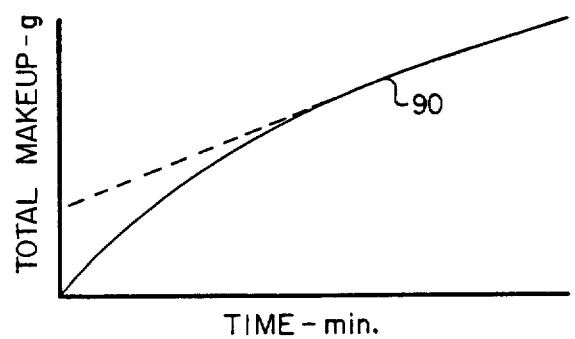
FIG. 4 is a diagram indicating the attrition rate of a typical particulate catalyst material.

FIG. 4 shows a typical plot of material in grams of the total makeup quantity versus time in minutes and the slope of the curve 90 indicates the rate of attrition of the specific type of particulate material being measured. The dimensions for the apparatus 10 and the test procedure, given by way of example hereinabove, may be modified to accommodate a particular type of material being tested, although the basic process involving continuous separation of fines and stabilizing the attrition rate or equilibrium by making additions of new prescreened material provides an improved method for determining attrition rates of particulate material.

The power input to the apparatus 10 can be measured calorimetrically, according to the following process. First, the housing 12 is artificially heated to a temperature considerably above ambient. Then, with the rotor turning and the air stream passing through the apparatus 10, but without any catalyst charge, therein, the rate of change of temperature with time is determined. The constant k in the equation $d(\Delta T)/\Delta t = -k(\Delta T - \Delta T_{eq})$ is calculated from data, where $\Delta T_{eq}$ is the temperature differential caused by the work done by the rotor on the air in the chamber 19. During a test involving a charge of catalyst or other particulate material, the value of $\Delta T - \Delta T_{eq}$ may be found by simply noting the final temperature attained by the apparatus 10. When this value is multiplied by the product of k times the total heat capacity C of the apparatus 10, the result is the amount of power being absorbed by the particulates.

The average age of the original material inventory is the inventory divided by the initial rate of fines production, while the average age of the new equilibrium material inventory is the inventory divided by the final rate of fines production. The average lifetime of both materials can be expressed either in terms of minutes in the chamber, or more fundamentally, in terms of the energy required to convert them into fines (kilowatt hours per ton).

Previous work indicates that the attrition per impact varies with the velocity to the 10/3 power. On this basis, attrition per unit energy (tons per kwh) would vary with velocity to the 4/3 power. The absolute attrition rate in a system utilizing the material being measured can be estimated from laboratory attrition rate data, provided that flow rates and velocities of the material in question can be found.

Although preferred embodiments of an apparatus and method in accordance with the present invention have been described in detail herein, those skilled in the art will recognize that various substitutions and modifications may be made to the specific embodiments described without departing from the scope and spirit of the invention as recited in the appended claims.

What I claim is:

1. Apparatus for determining the attrition rate of a quantity of particulate material comprising:
   a housing defining a chamber and including means forming a first opening for admitting particulate material to said chamber;
   impeller means disposed in said housing for impelling said material to exert impact forces on said material;
   means defining a second opening into said chamber for withdrawing attrited material from said chamber during operation of said impeller means the particulate material admitable through said first opening during operation of said impeller means;
   means for providing a flow of fluid through said chamber for permanently withdrawing said attrited material from said chamber during operation of said impeller means; and
   means for collecting a sample of attrited material withdrawn from said chamber for determining the rate of attrition of material in said chamber.

2. The apparatus set forth in claim 1 wherein:
   said means providing a flow of fluid includes vacuum pump means in fluid flow communication with said chamber by way of said second opening for withdrawing attrited material by imparting a flow of air through said chamber.

3. The apapratus set forth in claim 2 wherein:
   said means for collecting comprises a filter element interposed between said vacuum pump means and said chamber for collecting a sample of attrited material withdrawn from said chamber.

4. The apparatus set forth in claim 4 wherein:
   said impeller means includes a plurality of radially projecting impeller blades and shaft means for supporting said impeller blades, said impeller blades sweeping an arc which substantially envelopes said opening.

5. The apparatus set forth in claim 5 including:
   means defining a screen disposed across said second opening to prevent withdrawal of material from said chamber having a particle size greater than a predetermined. particle size comprising said fines.

6. The apparatus set forth in claim 6 wherein:
   said impeller blades are disposed adjacent said screen for creating turbulence across said screen during operation of said apparatus to prevent accumulation of particulate material on said screen having a particle size greater than that which will normally pass through said screen.

7. The apparatus set forth in claim 6 wherein:
   said housing comprises opposed sidewalls and a peripheral wall defining said chamber, said impeller means being disposed for rotation in said chamber in close proximity to said sidewalls and being mounted eccentrically with respect to a central longitudinal axis of said chamber.

8. The apparatus set forth in claim 1 wherein:
   said means defining said first opening comprises a hub portion of said housing for receiving a shaft of said impeller means and having said first opening formed in said hub portion for admitting material to said housing near the axis of rotation of said impeller means.

9. Apparatus for determining the attrition rate of a quantity of particulate material comprising:
   a housing defining a chamber and including means defining a first opening for admitting particulate material to said chamber and means defining a second opening for withdrawing attrited material or fines from said chamber;
   impeller means disposed in said housing for impelling said material to exert impact forces on said material;
   means in communication with said second opening for providing a flow of air from said chamber through said second opening for permanently withdrawing said attrited material from said chamber;
   motor means drivably connected to said impeller means for rotating said impeller means while withdrawing attrited material through said second opening during operation of said impeller means to deliver impact impelling forces to said material in said chamber the particulate material admitable through said first opening during operation of said impeller means; and
   means for collecting attrited material withdrawn from said chamber whereby the rate of attrition of said quantity of material in said chamber may be determined.

10. A method for determing the rate of attrition of a quantity of particulate material subject to impact forces during use comprising the steps of:
    providing means for imparting impact forces to a predetermined quantity of said particulate material, said means including a chamber for receiving said quantity of particulate material and means in said chamber for imparting said impact forces to said quantity of particulate material;
    operating said means for imparting impact forces to said quantity of particulate material while substantially continuously and permanently withdrawing fines generated by impacting said particulate material from said chamber;
    adding a quantity of makeup particulate material to said chamber;
    repeating the steps of withdrawing fines and adding makeup material so as to determine the attrition rate of the type of particulate material being measured.

11. The method set forth in claim 12 wherein:
the step of withdrawing fines from said chamber is carried out by conducting a flow of air through said chamber to entrain said fines in said flow of air and conducting said flow of air out of said chamber and to means for separating the fines from said air flow stream.

12. The method set forth in claim 11 including the step of:
providing means for screening said quantity of material in said chamber to prevent extraction of material from said chamber having a particle size greater than a predetermined size range during withdrawal of said fines.

13. A method for determing the rate of attrition of a quantity of particulate material subject to impact forces during use comprising the steps of:
providing means for operating on a predetermined quantity of said particulate material, said means including a chamber for receiving said quantity of particulate material and means in said chamber for imparting impact forces to said quantity of particulate material;
operating said means for imparting impact forces to said quantity of particulate material while substantially continuously withdrawing fines generated by impacting said particulate material from said chamber;
determining the mass of fines withdrawn from said chamber over a predetermined time period and adding a quantity of makeup particulate material to said chamber equal to the mass of fines withdrawn;
repeating the steps of withdrawing fines and adding makeup material until the rate of adding makeup material remains substantially constant so as to determine the attrition rate of the particulate material being measured.

14. A method for determining the rate of attribution of a quantity of particulate material subject to impact forces during use comprising the steps of:
providing means for imparting impact forces to a predetermined quantity of said particulate material, said means including a chamber for receiving said quantity of particulate material and means in said chamber for imparting said impact forces to said quantity of particulate material;
operating said means for imparting impact forces to said quantity of particulate material while substantially continuously withdrawing fines generated by impacting said particulate material from said chamber;
determining the mass of fines withdrawn from said chamber over a predetermined time period and adding makeup to material to said chamber corresponding to the mass of fines withdrawn over said predetermined time period;
repeating the steps of withdrawing fines and adding makup material until the rate of adding makeup material remains substantially constant so as to determine the attrition rate of the type of particulate material being measured.

15. A method for determining the rate of attrition of a quantity of particulate material subject to impact forces during use comprising the steps of:
providing means for imparting impact forces to a predetermined quantity of said particulate material, said means including a chamber for receiving said quantity of particulate material and means in said chamber for imparting said impact forces to said quantity of particulate material;
operating said means for imparting impact forces to said quantity of particulate material while substantially continuously withdrawing fines generated by impacting said particulate material from said chamber by conducting a flow stream of air through said chamber to entrain said fines in said flow stream and conducting said flow stream out of said chamber and to means for separating the fines from said flow stream;
adding a quantity of makeup particulate material to said chamber;
repeating the steps of withdrawing fines and adding makup material so as to determine the attrition rate of the type of particulate material being measured; and
measuring the temperature differential between the temperature of air flowing through said chamber and the ambient temperature and determining the energy input to said quantity of particulate material form the relationship $$\text{Power} = kC(\Delta T - \Delta Teq)$$

wherein k is a constant, $\Delta T$ is the temperature differential during a test, $\Delta Teq$ is the temperature differential resulting from operation of the apparatus on air only and C is the heat capacity of the means defining said chamber and its contents.

* * * * *